(12) United States Patent
Wellhoefer

(10) Patent No.: US 9,855,168 B2
(45) Date of Patent: Jan. 2, 2018

(54) NOZZLE UNIT FOR CROSS-LINKING OF EYE TISSUE

(71) Applicant: Wavelight Gmbh, Erlangen (DE)

(72) Inventor: Armin Wellhoefer, Schwaig (DE)

(73) Assignee: Wavelight GMBH, Erlangen (DE)

( * ) Notice: Subject to any disclaimer, the term of this patent is extended or adjusted under 35 U.S.C. 154(b) by 134 days.

(21) Appl. No.: 14/849,309

(22) Filed: Sep. 9, 2015

(65) Prior Publication Data

US 2016/0135989 A1    May 19, 2016

(30) Foreign Application Priority Data

Nov. 18, 2014   (DE) .................. 10 2014 016 990

(51) Int. Cl.

| | | |
|---|---|---|
| *A61F 9/00* | (2006.01) | |
| *A61N 5/06* | (2006.01) | |
| *A61M 11/02* | (2006.01) | |
| *A61F 9/007* | (2006.01) | |
| *A61F 9/008* | (2006.01) | |
| *A61J 1/14* | (2006.01) | |
| *A61H 35/02* | (2006.01) | |

(52) U.S. Cl.
CPC .......... *A61F 9/0026* (2013.01); *A61F 9/0079* (2013.01); *A61M 11/02* (2013.01); *A61N 5/062* (2013.01); *A61F 9/008* (2013.01); *A61H 35/02* (2013.01); *A61J 1/1443* (2013.01)

(58) Field of Classification Search
CPC ...... A61F 9/0026; A61F 9/0079; A61F 11/02; A61F 9/008; A61N 5/062; A61J 1/1443; A61H 35/02
See application file for complete search history.

(56) References Cited

U.S. PATENT DOCUMENTS

| | | | |
|---|---|---|---|
| 2007/0128343 A1 | 6/2007 | Chappa | |
| 2011/0301524 A1 | 12/2011 | Bueler et al. | |
| 2012/0203161 A1 | 8/2012 | Herekar | |
| 2013/0085459 A1* | 4/2013 | Voss .................. | A61B 3/10 |
| | | | 604/290 |
| 2013/0310728 A1 | 11/2013 | Seiler et al. | |

FOREIGN PATENT DOCUMENTS

| | | |
|---|---|---|
| EP | 2407132 A1 | 1/2012 |
| GB | 2465666 A | 6/2010 |
| WO | 2008008914 A2 | 1/2008 |
| WO | 2012154627 A2 | 11/2012 |
| WO | 2013059837 A2 | 4/2013 |
| WO | 2014114359 A1 | 7/2014 |

* cited by examiner

*Primary Examiner* — Edward Moran
*Assistant Examiner* — Courtney Fredrickson

(57) ABSTRACT

A nozzle unit for cross-linking of eye tissue is disclosed. The nozzle unit comprises a dosing device for providing a predefined dose of a photosensitizer, a pressure-generating device for generating a pressure in the dosing device, and an outlet nozzle for discharging the dose of the photosensitizer, in a puff-type manner and in the form of at least one stream or stream bundle, through an outlet opening of the outlet nozzle.

15 Claims, 5 Drawing Sheets

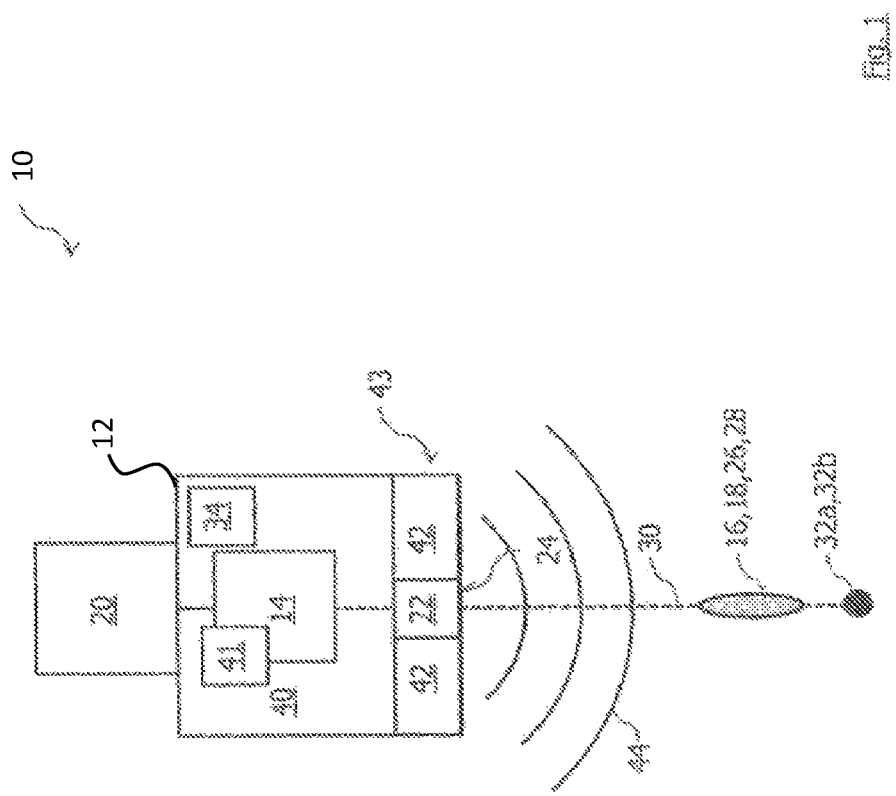

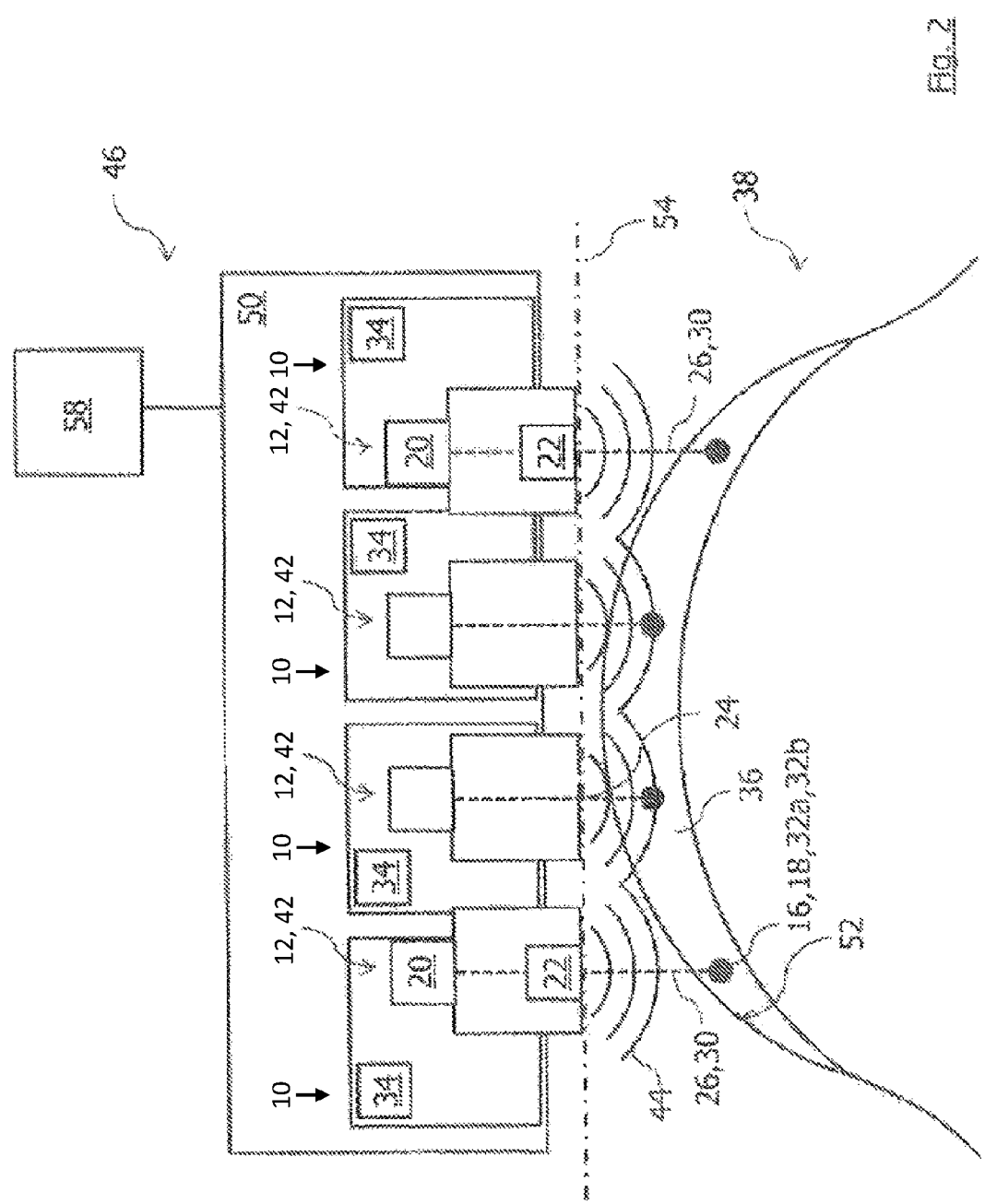

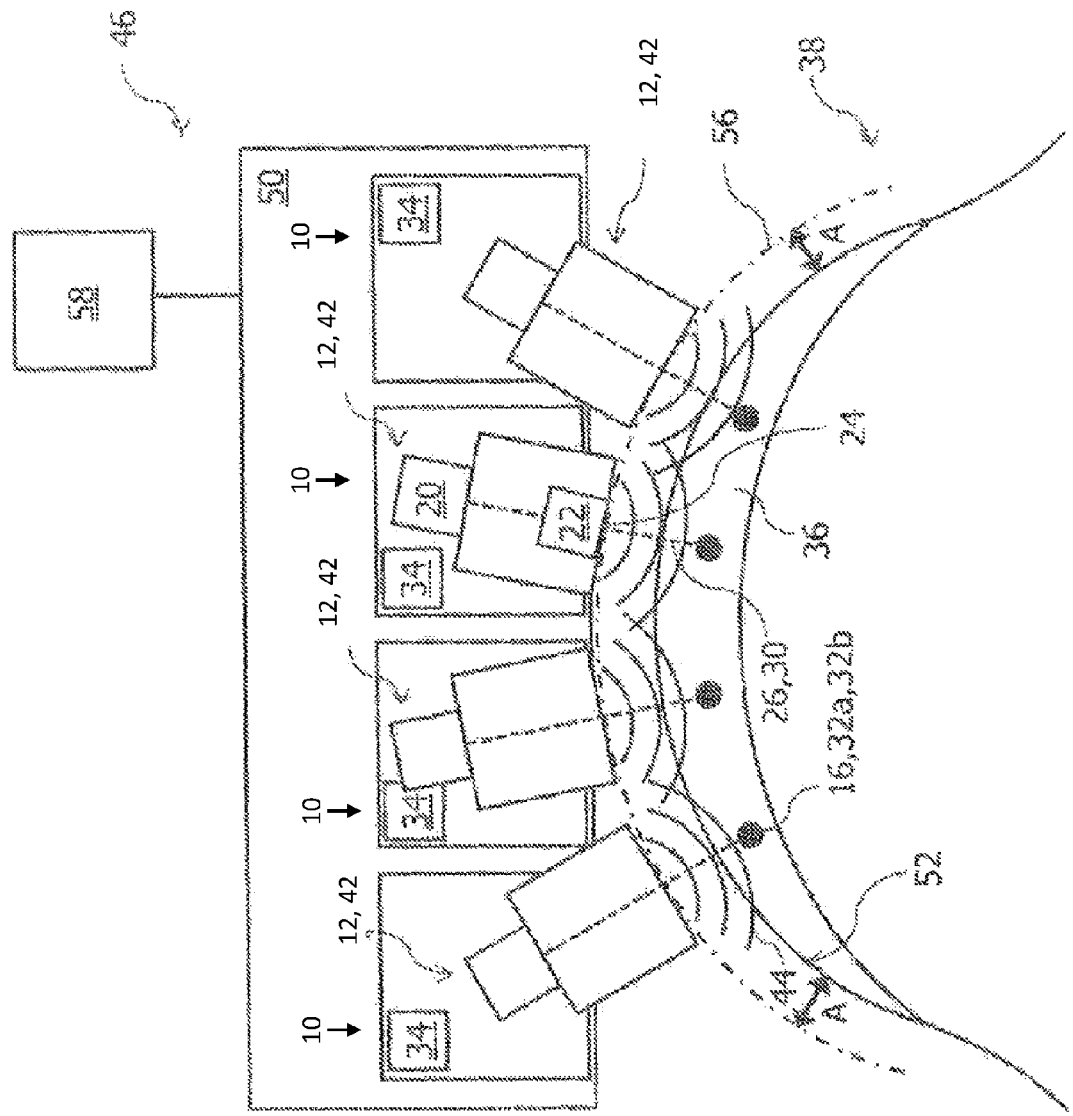

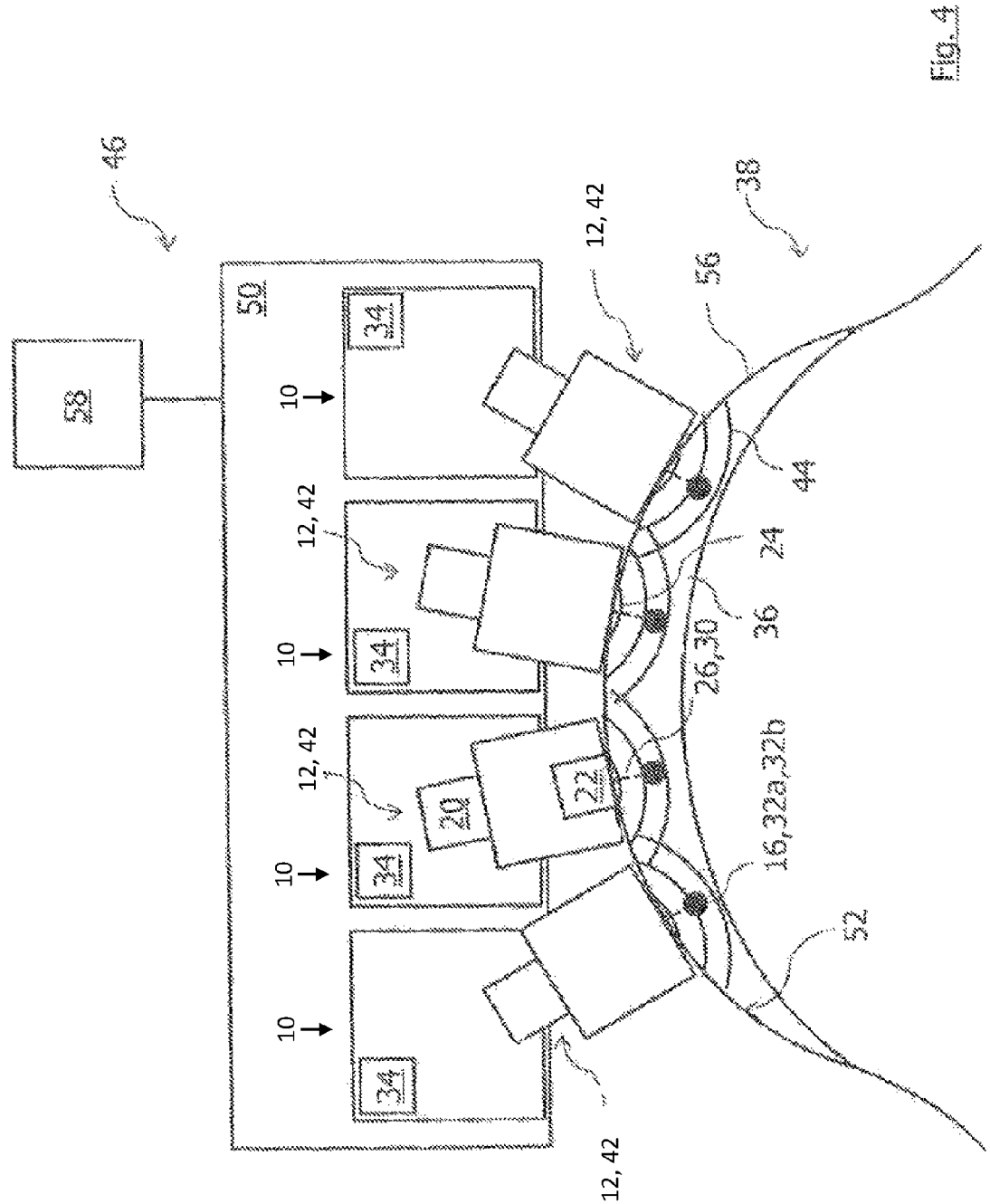

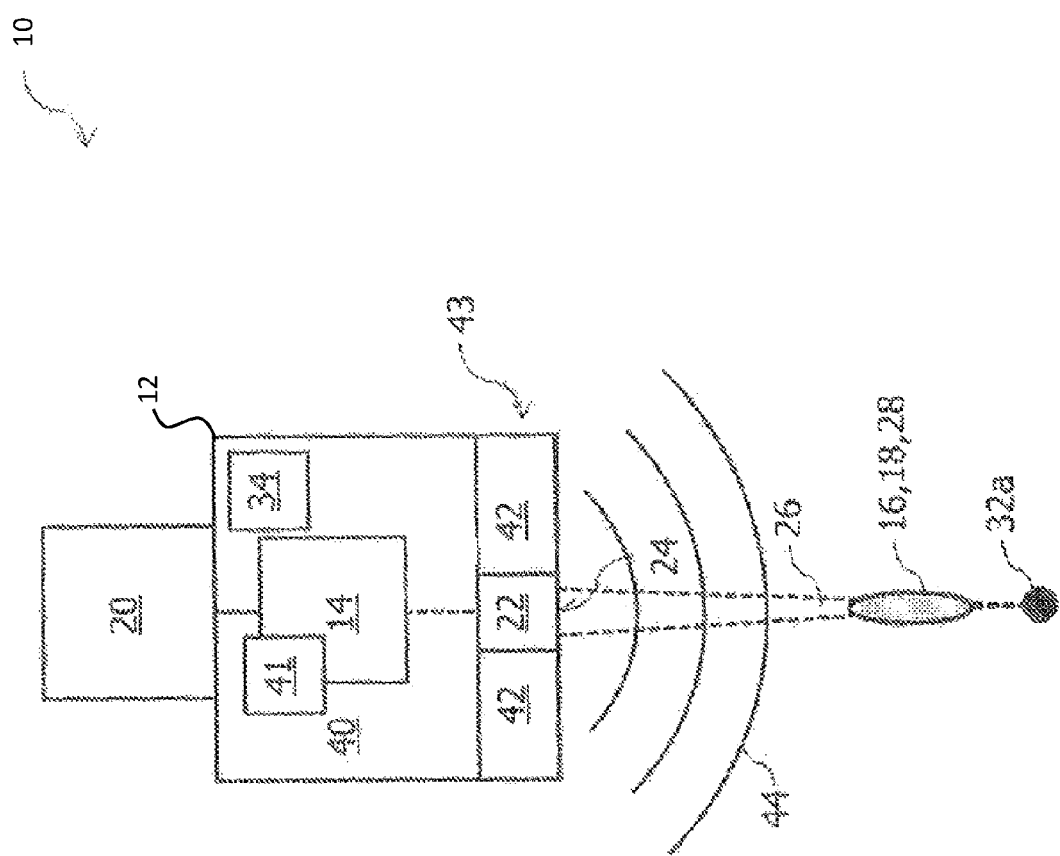

NOZZLE UNIT FOR CROSS-LINKING OF EYE TISSUE

TECHNICAL FIELD

The present disclosure relates to a nozzle unit for cross-linking of eye tissue, a unit for cross-linking of eye tissue having such a nozzle unit, and a device for treating an eye having such a nozzle unit and/or such a unit for cross-linking. The present disclosure further relates to a method for cross-linking of eye tissue.

BACKGROUND

In the field of ophthalmology, a so-called photosensitizer and electromagnetic radiation can be used to alter the biomechanical and biochemical properties of eye tissue, namely the cornea, for example, for therapeutic purposes.

The human eye is delimited by the outer coat of the eyeball. The intra-ocular pressure tensions the outer coat of the eyeball, which contains collagen, and gives the healthy eye its approximately spherical shape. In the rear region of the eye, the outer coat of the eyeball is formed by the white sclerotic coat (sclera). The cornea, which is permeable to visible light, is located in the anterior region. A deformation of the outer coat of the eyeball can be the cause of defective vision. For example, one form of short-sightedness, axial myopia, can result from a sclerotic axial elongation of the eye. An ellipsoidal surface of the cornea can lead to a form of astigmatism, which is referred to as keratoectasia. Keratoconus is a further disease of the cornea. Keratoconus involves an unnatural degeneration of the cornea, which can lead to a progressive thinning and conical deformation of the ocular cornea. As the convexity increases, the cornea becomes thinner, e.g., underneath the center, depending on the progression of the keratoconus, whereby the cornea can perforate and scar over. Visual acuity is permanently diminished as a result.

In order to treat an advanced case of keratokonus, the diseased cornea can be removed using the keratoplasty method and can be replaced with an allograft. Such an operation is an organ transplant, however, and has associated risks and complications. After a case of keratoconus has been treated, it may take years after the keratoplastic operation for eyesight to return to an acceptable level.

According to a different type of therapy, after the early detection of keratoconus, the keratoconus is treated by stabilizing the cornea by cross-linking a photosensitizer that has been applied onto and/or into the eye. The aforementioned treatment results in a photochemical, non-tissue abrading stabilization or alteration of the biomechanical and biochemical properties of the cornea.

A photosensitizer or a photosensitizer solution is first applied, e.g., as an active agent, into the eye tissue to be altered and is then exposed to the radiation of a light source. Electromagnetic radiation in the wavelength range from approximately 300 nm to 800 nm (UV-A radiation or visible light) can be used, for example, as the luminous radiation or primary radiation.

Possible photosensitizers that can be used are, for example, riboflavin (vitamin B2), lysyl oxidase, transglutaminase, sugar aldehydes, ethylcarbodiimide, glutaraldehyde, formaldehyde, or mixtures thereof, e.g., Karnovsky's solution. The photosensitizer can be in the form of a liquid and/or gaseous solution or a powder. In conventional techniques, the epithelium of the cornea can be at least partially removed, for example, by means of an alcohol-containing agent, or the flap (epithelium of the cornea with stromal tissue) can be folded open by means of a so-called flap cut, in order to enable a photosensitizer to freely penetrate the cornea, since, depending on the photosensitizer solution that is used, the epithelium of the cornea can be a barrier for the diffusion of the photosensitizer molecules into the corneal tissue. The removal of the epithelium, for example, using the alcohol-containing agent, is usually painful for the patient and the subsequent healing process is not always without complications.

According to a recent approach, in order to accelerate the healing process, at least one channel is cut in the eye tissue with the aid of laser radiation before the photosensitizer is applied, said channel being cut in the cornea or the stroma thereof, for example, and extending from the surface of the eye tissue into the interior thereof, for example. Next, the photosensitizer can be applied in drops onto the eye and can thereby be introduced through the channel that was cut out and can diffuse into the eye tissue. In an alternative embodiment, the photosensitizer can also be introduced into the eye tissue in a targeted manner by means of a cannula. Forming the flap or the at least one channel by means of an incision is still a surgical intervention in the eye tissue. The disadvantage thereof is that forming channels by cutting only enables channel-type regions of the eye tissue to be supplied with the active agent, since certain stabilization areas must remain between the channels in order prevent further weakening of the eye tissue. Therefore, the only way to apply the photosensitizer over the entire surface is to remove the epithelium by means of the alcohol-containing agent or by means of a flap cut, as described above. In addition, when drops are applied, the photosensitizer is usually dosed manually, which can result in dosage fluctuations that cannot be reproduced.

SUMMARY OF EXAMPLE EMBODIMENTS

In order to eliminate the aforementioned problems, examples of a nozzle unit for cross-linking of eye tissue is described. Said nozzle unit comprises a dosing device for providing a predefined dose of a photosensitizer and a pressure-generating device for generating a pressure in the dosing device. The nozzle unit further comprises at least one outlet nozzle having at least one outlet opening, wherein the outlet nozzle is configured to discharge the dose of the photosensitizer, in the manner of a puff or chermadic and in the form of a stream or a stream bundle, through the outlet opening of the outlet nozzle.

According to this nozzle unit, a predetermined dose of photosensitizer or photosensitizer solution is pressurized and is injected via the outlet opening of the outlet nozzle into the eye tissue, for example, into the cornea, e.g., into the stroma. It is therefore no longer necessary to first form a channel or a flap via incision, nor to remove the eye tissue in order to introduce the photosensitizer. Instead, the photosensitizer can be injected or introduced directly into the eye tissue without advance preparation. Since the puff-type or chermadic-type discharge of the dose of the photosensitizer also takes place in the form of a directed stream or stream bundle, the discharged dose of the photosensitizer corresponds to a spatially and temporally delineated, bundled packet, i.e., a photosensitizer-dose pulse, which proceeds along a propagation direction that is predefined (by the positioning, for example, i.e., the spatial arrangement and orientation of the outlet opening of the outlet nozzle). This permits precise dosing of the photosensitizer. In this sense, the nozzle unit can be referred to as a nozzle unit for preparing an eye for cross-linking of eye tissue. Such a delineated and bundled dosing packet also permits accurate local positioning of the discharged dose of photosensitizer in the eye tissue. Finally, since the photosensitizer is discharged in the form of a stream or a stream bundle, there is no need for external guidance of the photosensitizer dose in order to bundle and delineate the photosensitizer dose, by means of a cannula or an injection device, for example. In this sense, the nozzle unit therefore makes it possible to inject the photosensitizer without a cannula and even without contact between the eye tissue and the nozzle unit. In one alternative embodiment, an embodiment can also be included which, depending on the nozzle unit, is contact-based, i.e., has direct contact with the eye. The latter is feasible, for example, although not exclusively so, in the case of a nozzle unit formed as a hand applicator, wherein a pressure-compensation spring can then be provided. In addition to placing the nozzle onto the eye, it is also feasible for the nozzle unit to apply a pressure onto the eye tissue, e.g., in a range of 20 mmHg to 60 mmHg, for example in the range of 20 mmHg to 30 mmHg, for instance in the range of 30 mmHg to 50 mmHg, for example, with the use of a nozzle attachment, similar to a so-called application cone. In a further embodiment, the nozzle unit can be suctioned onto the eye using vacuum in a range of 500 mbar to 750 mbar.

In certain embodiments, the outlet nozzle can be configured, for example, as a micro-nozzle or a micro-outlet nozzle. In addition, the outlet nozzle can be configured to spatially focus the discharged stream bundle or the stream. To this end, at least one outlet nozzle and, for example, the outlet opening thereof, can be geometrically configured and dimensioned accordingly. For example, it is feasible to arrange a plurality of micro-nozzles in a certain angle relative to one another or, for example, in a circular, polygonal, or otherwise geometric arrangement.

In this case, the stream or the discharged stream bundle of the photosensitizer dose tends to move toward a predefined spatial point, wherein the lateral expansion tapers successively, for example in the case of a stream bundle. This makes it possible to even more precisely position the discharged photosensitizer dose in the eye tissue.

The outlet opening of the outlet nozzle can be circular and can have a diameter, for example, of approximately 30 μm to 300 μm, e.g., 150 μm. Any other geometric shape of the outlet opening is also feasible, however, such as, for example, strip-shaped, polygonal or oval.

In certain embodiments, the nozzle unit can comprise a control device. The control device is configured, for example, to set the pressure generated by the pressure-generating device, for example, within the dosing device. To this end, the control device can be configured to set the pressure, for example, on the basis of characteristics of the eye to be treated, such as the geometry, position, orientation and/or robustness of the point in the eye to be treated, in order to obtain an exiting velocity of 100 to 200 m/s. As an alternative or in addition, the control device can be configured to set the pressure, for example, on the basis of properties of the photosensitizer, such as weight and/or size of the active agent molecule and/or the viscosity of the solution, properties of the dosing device, such as the amount, weight and/or volume of the predefined photosensitizer dose, properties of the pressure-generating device, such as the maximum pressure that can be generated and/or the duration of the pressure provided, properties of the outlet nozzle, such as the diameter, exit surface, positioning and/or orientation of the outlet opening and/or geometry of the outlet nozzle. For example, the control device can be configured to set the pressure generated by the pressure-generating device such that the stream bundle discharged by the outlet nozzle penetrates corneal eye tissue and, in fact, for example, up to or only up to a predefined penetration depth within the eye tissue, e.g., the stroma. The penetration depth into the tissue depends, for example, on the nozzle diameter, e.g., in the range of approximately 20 μm to 300 μm, such as 30 μm, for example, and depends, for example, on the amount of injected fluid, for example, 0.01 ml to 0.5 ml, such as 0.07 ml, and, for example, on the rate of the injection, for example, of approximately 100 m/s to 200 m/s, such as in the range of 140 m/s to 160 m/s.

In certain embodiments, the nozzle unit can precisely introduce a desired dose of photosensitizer at any position in the eye tissue in order to supply certain points with more photosensitizer than other points, for example, depending on the anatomy and diagnosis of the diseased eye. It is therefore possible to apply a predefined pattern comprising a plurality of photosensitizer doses within the eye tissue depending on the diagnosis and, therefore, to individually adapt said predefined pattern to the treatment requirements of the eye of a particular patient. The control device can be used to set not only the injection pressure of the discharged photosensitizer dose, but also the instant of release and/or injection duration. By ejecting the photosensitizer it is possible to apply a pattern in the eye tissue. The pattern is defined on the basis of diagnostic data, for example, a topographical evaluation of the eye and the local concentration of active agent recommended by the physician and/or on the basis of computation. This also makes it possible to distribute the photosensitizer over a large surface area of the eye.

The control device can be configured to set the pressure generated by the pressure-generation device in the range of approximately 100 kPa to approximately 900 kPa. In order to obtain the desired pressure setting, the nozzle unit can comprise a pressure-measuring sensor, which is connected to the control device, and/or a valve, which can be switched between an opened position and a closed position, for example, by means of the control device.

In certain embodiments, the nozzle unit can comprise a reservoir for a photosensitizer or a supply of photosensitizer. In one alternative embodiment, a magazine comprising a plurality of ampules is provided, in order to provide different active agents and/or concentrations.

In order to provide a predefined dose, the dosing device can therefore be repeatedly and successively loaded with the same dose or different doses of the photosensitizer by means of a suitable loading device of the nozzle unit. It is therefore possible to dispense not only a single dose of photosensitizer, but also a salve or an entire series of photosensitizer doses. This makes it possible to apply a predefined pattern using only a single nozzle unit.

In certain embodiments, a unit for cross-linking of eye tissue can comprise one or more of the above-described nozzle units. In addition, the unit can comprise at least one light source for emitting electromagnetic radiation. The light source is configured, for example, to cross-link eye tissue into which photosensitizer has been introduced by curing the photosensitizer. The light source can be configured, for example, as a slit lamp or in combination with a slit lamp.

In certain embodiments, the nozzle unit for injecting the photosensitizer and the light source for cross-linking of eye tissue by curing the photosensitizer injected by means of the nozzle unit can be combined in one overall unit. This makes it possible to implement an automated procedure for introducing the photosensitizer in advance and then curing the photosensitizer without the need to switch back and forth between a plurality of devices. The result is a shorter treatment period and, therefore, less stress on the patient. The unit also makes it possible to implement a fixed spatial arrangement of the nozzle unit relative to the light source. This makes it possible to orient the light beam bundle emitted by the light source relative to the photosensitizer stream bundle discharged by the nozzle unit and thereby precisely radiate a point in the eye tissue to which photosensitizer has been applied. In this sense, the unit for cross-linking of eye tissue can also be referred to simply as a cross-linking unit.

In certain embodiments, a device for treating an eye can comprise one or more of the above-described nozzle units. As an alternative or in addition thereto, the device for treating an eye can comprise one or more of the above-described units for cross-linking. The device for treating an eye can also comprise a positioning device. The positioning device is configured, for example, to position the outlet nozzle of the at least one nozzle unit or the at least one unit for cross-linking relative to the eye to be treated. To this end, the outlet nozzle can be disposed on the device so as to be spatially displaceable and/or rotatable by means of the positioning device. If the device for treating an eye comprises at least two outlet nozzles, the positioning device can also be configured to spatially position the outlet nozzles among one another, i.e., relative to one another.

As a result, at least one outlet nozzle can aim for or approach any point on the cornea, e.g., by means of a servomotor device or an equivalent, in order to apply a photosensitizer dose there. It is also possible to position the at least one outlet nozzle relative to the eye such that a certain, predefined separation is maintained between the outlet opening of the at least one outlet nozzle and the eye, for example, a corneal surface of the eye. It is therefore possible to treat the eye at a distance, i.e., without direct contact between the device and the eye, in order to avoid stressing the eye with the device itself. Sterilization is therefore also not required. For a person known in the art is it needless to say that the eye needs to be opened by a speculum to avoid the winking reflex of the eye lid.

In certain embodiments, the positioning device can be further configured, for example, to spatially position the outlet nozzles relative to one another such that the outlet openings thereof are arranged in a flat plane and, for example, the discharged stream bundles can extend substantially parallel to one another. The positioning device can also be configured to spatially position the outlet nozzles relative to one another such that the outlet openings thereof are arranged in a curved plane, which is adapted to the contour of the eye to be treated, and, for example, the discharged stream bundles can enter the eye substantially perpendicularly to the contour of the eye to be treated.

In certain embodiments, the photosensitizer can be ejected from each one of the plurality of nozzle units and thereby apply a complete pattern in the eye tissue. The pattern is defined on the basis of diagnostic data, for example, a topographical evaluation of the eye and the local concentration of active agent recommended by the physician and/or on the basis of computation. This also makes it possible to distribute the photosensitizer over a large surface area of the eye. In addition, the outlet nozzles can be spatially positioned in such a way that the location of the photosensitizer dose to be applied or the dosing pattern to be applied can be adjusted, for example, with consideration for the individual geometry of the eye to be treated.

In certain embodiments, the device can comprise a computer unit, which is configured to move the positioning device from at least one first state, in which the outlet opening of the outlet nozzle or the outlet openings of the outlet nozzles are spatially positioned in a first predefined arrangement relative to the eye to be treated, into at least one second state, in which the outlet opening of the outlet nozzle or the outlet openings of the outlet nozzles are spatially positioned in a second predefined arrangement relative to the eye to be treated, wherein the first predefined arrangement and the second predefined arrangement are different. It is possible to switch back and forth between a spatial positioning in which the outlet openings are disposed in a flat plane and, for example, the discharged stream bundles extend substantially parallel to one another, and a spatial position in which the outlet openings are disposed in a curved plane, which is adapted to the contour of the eye to be treated, and, for example, in which the discharged stream bundles enter the eye substantially perpendicularly to the contour of the eye to be treated.

In certain embodiments, the nozzle unit, the unit for cross-linking, or the device for treating an eye can be configured as a manual applicator. In this case, a computer unit for positioning is not necessary under certain circumstances, namely, for example, when the positioning of one outlet opening of an outlet nozzle or a plurality of outlet openings is carried out manually.

In certain embodiments, the nozzle unit, the unit for cross-linking, or the device for treating an eye can comprise an evaluation unit for calculating a distribution of active agent and/or a diagnostic device for recording diagnostic data. The diagnostic device can be configured, for example, as a device for optical coherence tomography (in short: OCT device), as a pachymeter and/or a topolyzer. The evaluation unit can be configured to calculate the distribution of active agent on the basis of diagnostic data, for example on the basis of the diagnostic data recorded by the diagnostic device. The control device can be configured to control the at least one nozzle unit on the basis of diagnostic data, for example on the basis of the diagnostic data recorded by the diagnostic device. For example, the control device can be configured to control the at least one nozzle unit on the basis of a pattern created by the evaluation unit. In this case, an individual pattern can be defined, for example, on the basis of data from diagnostic devices, for example, OCT, a pachymeter, a topolyzer, etc., and evaluated by the evaluation unit and transferred to the control device in advance.

Diagnostic data can therefore be evaluated in order to exactly adjust a dose of the photosensitizer and a location for the application depending on the individual biomechanical characteristics of the patient's eye.

In certain embodiments, the nozzle unit, the unit for cross-linking, or the device for treating an eye can comprise an eye-tracking device. The eye-tracking device can be configured as a so-called eye-tracker. The eye-tracking device can be configured to detect a position and/or an orientation of the eye to be treated relative to the at least one nozzle unit. The control device can be configured to control the at least one nozzle unit on the basis of the position detected by the eye-tracking device and/or the orientation of the eye to be treated.

It is thereby possible to apply active agent on a moving eye in a targeted manner. In certain embodiments, a method for cross-linking of eye tissue comprises the steps of
  providing a predefined dose of a photosensitizer in a dosing device,
  generating a pressure in the dosing device, and
  discharging the dose of the photosensitizer, in a puff-type or chermadic-type manner and in the form of at least one stream or at least one stream bundle, through an outlet opening of an outlet nozzle. In this sense, the method can be referred to as a method for preparing an eye for cross-linking of eye tissue.

Further specific embodiments of the method for cross-linking of eye tissue are set forth in the dependent claims.

To the extent that a method for cross-linking of eye tissue or individual steps of this method is/are described in this disclosure, the method or individual steps of the method can be carried out by an appropriately configured device or a part of such a device. The same applies for the explanation of the mode of operation of a device or part of a device that carries out method steps, even if the method steps per se are not explicitly mentioned.

BRIEF DESCRIPTION OF FIGURES

Specific embodiments of the disclosure will be explained in more detail with reference to the attached schematic drawings, wherein FIG. 1 shows a schematic cross-sectional depiction of a unit for cross-linking of eye tissue, comprising a nozzle unit, FIG. 2 shows a schematic depiction of a device for treating an eye, comprising nozzle units, wherein the outlet nozzles of the nozzle units are located in a first spatial positioning, FIG. 3 shows a schematic depiction of the device from FIG. 2, wherein the outlet nozzles of the nozzle units are located in a second spatial positioning, FIG. 4 shows a schematic depiction of the device from FIGS. 2 and 3, wherein the outlet nozzles of the nozzle units are located in a third spatial positioning, and FIG. 5 shows a schematic cross-sectional depiction of a unit for cross-linking of eye tissue, comprising a nozzle unit, in the case of which a stream bundle is discharged in a spatially focussed manner.

DETAILED DESCRIPTION OF EXAMPLE EMBODIMENTS

FIG. 1 shows a unit 10 for cross-linking of eye tissue. The unit 10 comprises a nozzle unit 12 for cross-linking of eye tissue.

The nozzle unit 12 comprises a dosing device 14 for providing a predefined dose 16 of a photosensitizer 18, and comprises a pressure-generating device 20, which is connected to the dosing device 14, for generating a pressure in the dosing device 14. The nozzle unit 12 further comprises an outlet nozzle 22 having an outlet opening 24, wherein, due to the pressure generated by the pressure-generating device 20, the outlet nozzle 22 discharges the dose 16 of the photosensitizer 18, in the manner of a puff or chermadic and in the form of a stream bundle 26, through the outlet opening 24 of the outlet nozzle 22. The outlet opening 24 is circular, for example, and has a diameter of approximately 150 μm, for example.

A desired, predetermined dose 16 of photosensitizer 18 can therefore be injected into the eye tissue, for example, into a cornea. Since the puff-type or chermadic-type administration of the dose 16 of the photosensitizer 18 takes place in the form of a stream bundle 26, the administered dose 16 of the photosensitizer 18 corresponds to a delineated, bundled packet 28, i.e., a photosensitizer-dose pulse, which proceeds along a propagation direction 30 that is predefined by the positioning, i.e., the spatial arrangement and orientation of the outlet opening 24. This makes it possible to precisely dose the photosensitizer 18. Such a delineated and bundled packet 28 also makes it possible to exactly position the discharged photosensitizer dose 16 in the eye tissue. In addition, since the photosensitizer 18 is discharged in the form of a stream bundle 26, external guidance of the photosensitizer dose 16 is not required in order to bundle and delimit the photosensitizer dose 16, for example, by means of a cannula. In this sense, the nozzle unit 12 makes it possible to inject the photosensitizer 18 without a cannula and even contactlessly with respect to the eye tissue.

The nozzle unit 12 also comprises a reservoir 40 having a supply of photosensitizer 18 and a suitable loading device 41 for repeatedly and successively loading the dosing device 14 with photosensitizer 18, in order to provide a predefined dose 16. It is therefore possible to dispense not only a single photosensitizer dose 16, but also a salve or an entire series of photosensitizer doses 16.

The outlet nozzle 22 is configured as a micro-nozzle, for example, and is set up to spatially focus the discharged stream bundle 26 onto a predefined spatial point 32a, i.e. a focal point, as shown in FIG. 5 as an example. The discharged stream bundle 26 of the photosensitizer dose 16 thereby tends to move toward the predefined spatial point 32a, wherein the lateral expansion of the stream bundle 26 successively tapers. This makes it possible to even more precisely position the discharged photosensitizer dose 16 in the eye tissue.

The nozzle unit 12 also comprises a control device 34. The control device 34 is configured to set the pressure in the range, for example, of approximately 100 kPa to approximately 900 kPa generated by the pressure-generating device 20 on the basis of characteristics of the eye to be prepared such as, for example, geometry, position, orientation and robustness of the point in the eye to be prepared, properties of the photosensitizer 18 such as the weight and size of the active agent molecule or the viscosity of the photosensitizer solution, properties of the dosing unit 14 such as the amount, weight and volume of the predefined photosensitizer dose 16, properties of the pressure-generating device 20 such as the maximum pressure that can be generated and the duration of the pressure provided, and properties of the outlet nozzle 22 (such as diameter, outlet surface, positioning and/or orientation of the outlet opening 24 and geometry of the outlet nozzle 22. The control unit can set not only the injection pressure of the dose 16, but also the injection duration thereof.

The control device 34 sets the pressure generated by the pressure-generating device 20 such that the stream bundle 26 discharged from the outlet nozzle 22 penetrates corneal eye tissue 36 up to and, in fact, only up to a predefined penetration depth 32b within the eye tissue 36. As a result, the nozzle unit 12 can precisely introduce the desired dose 16 of photosensitizer 18 at any position in the eye tissue 36 and thereby apply a predefined pattern comprising a plurality of photosensitizer doses 16 within the eye tissue 36 (shown in FIGS. 2 to 4), wherein the pattern is individually adapted to the requirements for the treatment of the eye 38 of the particular patient. The individual pattern can therefore be defined, for example, on the basis of data from diagnostic devices, e.g., OCT, a pachymeter, a topolyzer, etc., and can be evaluated by the evaluation unit and transferred to the control device 34 in advance. Diagnostic data can therefore be evaluated in order to exactly adjust the dose 16, e.g., of the photosensitizer, and exactly adjust the location 32b for the application depending on the individual biomechanical characteristics of the patient's eye.

The unit 10 for cross-linking can comprise at least one nozzle unit 12. The unit 10 also comprises a light source 42 or even a plurality of light sources 42. The light source(s) 42 is/are configured as a slit lamp 43, for example, or form one part of a slit lamp. Every light source 42 is configured to cross-link the eye tissue 36 (shown in FIGS. 2 to 4) into which the photosensitizer 18 has been introduced by curing the photosensitizer 18. The nozzle unit 12 for injecting the photosensitizer 18 and the light source 42 for cross-linking of eye tissue by curing the photosensitizer 18 injected by means of the nozzle unit 12 are therefore combined in one unit 10. This makes it possible to implement an automated procedure for introducing the photosensitizer 18 into the eye tissue 36 (shown in FIGS. 2 to 4) in advance and then curing the photosensitizer 18 using only one device 10. The result is a shorter treatment period and, therefore, less stress on the patient. The unit 10 also makes it possible to obtain a fixed spatial arrangement of the nozzle unit 12 relative to the light source 42. This makes it possible to orient the light beam bundle 44 emitted from the light source 42 relative to the photosensitizer stream bundle 26 discharged by the nozzle unit 12 and thereby precisely radiate a point in the eye tissue 36 (shown in FIGS. 2 to 4) to which photosensitizer 18 has been applied.

FIGS. 2 to 4 shows schematic description of a device for treating an eye with a unit 10 for cross-linking of eye tissue. In the example shown, the device 46 comprises four nozzle units 12. It is also feasible, however, for the device 46 to comprise only one nozzle unit 12 and/or the unit 10 for cross-linking or any number of nozzle units 12 and/or units 10 for cross-linking.

The device 46 may also comprises a positioning device 50. The positioning device 50 is configured to position the outlet nozzles 22, more specifically the outlet openings 24, relative to the patient's eye 38 to be treated. To this end, every outlet nozzle 22 is disposed on the device 46 so as to be spatially displaceable and rotatable by means of the positioning device 50. The positioning device 50 is also configured to spatially position the outlet nozzles 22, more specifically the outlet openings 24, among one another, i.e., relative to one another.

It is therefore possible to dispose the outlet nozzle 22 of each nozzle unit 12 relative to the patient's eye 38 with any spatial arrangement and orientation. This makes it possible, for example, to move the outlet nozzle 22 toward any point on the eye tissue 36, e.g., the cornea, in order to apply a photosensitizer dose 16 there.

It is also possible to position an outlet nozzle 22 relative to the patient's eye 38 such that a certain predefined separation A is maintained between the outlet opening 24 of the (or of every) outlet nozzle 22 and the patient's eye 38, more specifically the corneal surface 56 to be treated (see FIG. 3). It can thereby be ensured that the patient's eye 38 can be treated without direct contact between the nozzle units 12 and the patient's eye 38.

As shown in FIG. 2, for example, the positioning device 50 can be configured to spatially position the outlet nozzles 22 relative to one another such that the outlet openings 24 are disposed in a flat plane 54 and the discharged stream bundles 26 extend parallel to one another along the propagation directions 30 thereof.

As shown in FIG. 3 or 4, for example, the positioning device 50 can also be configured, however, to spatially position the outlet nozzles 22 relative to one another such that the outlet nozzles 24 are disposed in a curved plane 56, and such that the discharged stream bundles 26 enter the patient's eye 38 along the propagation direction 30 thereof, perpendicularly to the contour 52 of the patient's eye 38 to be treated.

As shown in FIG. 4, for example, the positioning device 50 can additionally be configured to spatially position the outlet nozzles 22 relative to one another such that the outlet nozzles 24 are disposed in a curved plane 56 adapted to the contour 52 of the eye 38 to be treated.

As a result, a complete pattern can be applied in the eye tissue 36 with only one shot of the photosensitizer 18 from each nozzle unit 12. This makes it possible to distribute the photosensitizer 18 over a large surface area of the patient's eye 38. In addition, the outlet nozzles 12 can be spatially positioned in such a way that the location of the photosensitizer dose 16 to be applied can be adjusted and, in fact, with consideration for the individual geometry of the patient's eye to be treated.

The device 46 can comprise a computer unit 58, which is configured to move the positioning device 50 from a first state, in which the outlet openings 24 are spatially positioned in a first predefined arrangement (as shown in FIG. 2, for example) relative to the eye 38 to be treated, into a second state, in which the outlet openings 24 are spatially positioned in a second predefined arrangement relative to the patient's eye 38 to be treated, wherein the first predefined arrangement and the second predefined arrangement are different. The computer unit 58 can be connected to the device 46 or can be integrated within said device.

It is therefore possible, for example, to switch back and forth between the one spatial positioning, in which the outlet openings 24 are disposed in a flat plane 54 and the discharged stream bundles 26 extend parallel to one another along the propagation direction 30 thereof (see FIG. 2), and a spatial position in which the outlet openings 24 are disposed in a curved plane 56, which is adapted to the contour of the eye 38 to be treated, and in which the discharged stream bundles 26 enter the patient's eye 38 along the propagation direction 30 thereof, perpendicularly to the contour of the patient's eye 38 to be treated.

Unless expressly described otherwise, identical reference signs in the figures stand for identical or identically acting elements. In addition, any combination of the features depicted in the figures is feasible.

The invention claimed is:

1. A nozzle device comprising:
    at least two nozzle units for cross-linking of an eye tissue of an eye, each nozzle unit in the at least two nozzle units comprising:
        a dosing device configured to provide a predefined dose of a photosensitizer,
        a pressure-generating device configured to generate a pressure in the dosing device, and
        at least one outlet nozzle configured to discharge the dose of the photosensitizer, in a puff-type manner and in the form of at least one stream or stream bundle, through an outlet opening of the outlet nozzle; and
    a nozzle positioning device for a spatial positioning of each of the outlet nozzles of the at least two nozzle units relative to the eye to be treated.

2. The nozzle device according to claim 1, wherein each outlet nozzle is configured to spatially focus the discharged stream or the discharged stream bundle.

3. The nozzle device according to claim 1, wherein each nozzle unit further comprises a control device configured to set the pressure generated by each pressure-generating device.

4. The nozzle device according to claim 1, further comprising an evaluation unit configured to calculate a distribution of active agent on the basis of diagnostic data.

5. The nozzle device according to claim 1, further comprising an eye-tracking device configured to apply active agent on a moving eye in a targeted manner.

6. The nozzle device according to claim 3, wherein the control device is configured to set the pressure generated by each pressure-generating device such that the stream or the stream bundle discharged by each outlet nozzle penetrates corneal eye tissue up to a predefined penetration depth.

7. The nozzle device according to claim 1, wherein each nozzle unit further comprises a reservoir having a supply of photosensitizer.

8. The nozzle device according to claim 1, further comprising at least one light source configured to cross-link eye tissue by curing the photosensitizer introduced into the eye tissue.

9. The nozzle device according to claim 1,
wherein the positioning device is configured to spatially position each of the outlet nozzles relative to one another.

10. The nozzle device according to claim 1, wherein the positioning device is configured to spatially position the outlet nozzles relative to one another with an eye-tracking device, such that the outlet openings are arranged in a flat plane and the discharged streams or stream bundles extend substantially parallel to one another.

11. The nozzle device according to claim 1, wherein the positioning device is configured to spatially position the outlet nozzles relative to one another such that the outlet openings are arranged in a curved plane adapted to the contour of the eye to be treated, such that the discharged streams or stream bundles can enter the eye substantially perpendicularly to the contour of the eye to be treated.

12. A method for cross-linking eye tissue of an eye, comprising:

arranging at least two nozzle units for cross-linking the eye tissue of the eye within a nozzle positioning device, wherein each of the at least two nozzle units comprises at least one outlet nozzle configured to be spatially positioned relative to the eye to be treated, a dosing device configured to provide a predefined dose of a photosensitizer, and a pressure-generating device;

providing a predefined dose of a photosensitizer in the dosing devices of the at least two nozzle units;

generating, by the pressure-generating device, a pressure in the dosing devices of the at least two nozzle units; and discharging the dose of the photosensitizer, in a puff-type manner and in the form of at least one stream or stream bundle, through an outlet opening of each of the at least one outlet nozzles of the at least two nozzle units to the eye tissue of the eye.

13. The method according to claim 12, wherein the discharged stream or the discharged stream bundle is spatially focused.

14. The method according to claim 13, wherein the generated pressure can be set such that the discharged stream or the discharged stream bundle penetrates corneal tissue up to a predefined penetration depth.

15. The method according to claim 12, wherein the positioning device is configured to spatially position the outlet nozzles relative to one another such that the outlet openings are arranged in a curved plane adapted to the contour of the eye to be treated, such that the discharged streams or stream bundles can enter the eye substantially perpendicularly to a contour of the eye to be treated.

* * * * *